United States Patent
Inokuchi

(10) Patent No.: US 9,422,403 B2
(45) Date of Patent: Aug. 23, 2016

(54) WATER-ABSORBABLE SILICONE RUBBER PARTICLES AND METHOD FOR PRODUCING SAME

(71) Applicant: SHIN-ETSU CHEMICAL CO., LTD., Tokyo (JP)

(72) Inventor: Yoshinori Inokuchi, Annaka (JP)

(73) Assignee: SHIN-ETSU CHEMICALS CO., LTD., Tokyo (JP)

( * ) Notice: Subject to any disclaimer, the term of this patent is extended or adjusted under 35 U.S.C. 154(b) by 50 days.

(21) Appl. No.: 14/389,937

(22) PCT Filed: Feb. 21, 2013

(86) PCT No.: PCT/JP2013/054307
§ 371 (c)(1),
(2) Date: Oct. 1, 2014

(87) PCT Pub. No.: WO2013/153858
PCT Pub. Date: Oct. 17, 2013

(65) Prior Publication Data
US 2015/0050498 A1    Feb. 19, 2015

(30) Foreign Application Priority Data
Apr. 10, 2012  (JP) .................... 2012-088884

(51) Int. Cl.
| | |
|---|---|
| C08G 77/08 | (2006.01) |
| C08G 77/46 | (2006.01) |
| C08L 71/00 | (2006.01) |
| A61K 8/894 | (2006.01) |
| C08G 77/14 | (2006.01) |
| A61Q 1/02 | (2006.01) |
| A61Q 15/00 | (2006.01) |
| A61K 8/02 | (2006.01) |
| C08G 77/12 | (2006.01) |

(52) U.S. Cl.
CPC ............. *C08G 77/08* (2013.01); *A61K 8/025* (2013.01); *A61K 8/894* (2013.01); *A61Q 1/02* (2013.01); *A61Q 15/00* (2013.01); *C08G 77/14* (2013.01); *C08G 77/46* (2013.01); *C08L 71/00* (2013.01); *A61K 2800/412* (2013.01); *C08G 77/12* (2013.01); *Y10T 428/2982* (2015.01)

(58) Field of Classification Search
CPC ........ C08G 77/46; C08G 77/14; C08G 77/12; C08G 77/08; C08L 71/00; C08L 83/04; A61K 8/894; A61K 8/025; A61K 2800/412; A61Q 1/02; A61Q 15/00; C08K 5/06; C08K 5/56; Y10T 428/2982
USPC ............................. 428/402; 528/15
See application file for complete search history.

(56) References Cited

U.S. PATENT DOCUMENTS

| | | | | |
|---|---|---|---|---|
| 5,236,986 A | * | 8/1993 | Sakuta | A61K 8/894 524/267 |
| 5,412,004 A | * | 5/1995 | Tachibana | A61K 8/06 514/844 |
| 5,837,793 A | * | 11/1998 | Harashima | C08J 3/12 524/588 |
| 6,503,519 B1 | * | 1/2003 | Sakuta | A61K 8/28 424/401 |

FOREIGN PATENT DOCUMENTS

| | | |
|---|---|---|
| EP | 0 001 162 B1 | 12/1982 |
| JP | 54-46842 A | 4/1979 |
| JP | 4-272932 * | 9/1992 |
| JP | 4-272932 A | 9/1992 |
| JP | 6-040847 * | 2/1994 |
| JP | 6-40847 A | 2/1994 |
| JP | 9-136813 A | 5/1997 |
| JP | 9136813 * | 5/1997 |
| JP | 9-151126 * | 6/1997 |
| JP | 9-151126 A | 6/1997 |
| JP | 9-255793 A | 9/1997 |
| JP | 9-255794 A | 9/1997 |
| JP | 9-316493 A | 12/1997 |
| JP | 2001-002555 * | 1/2001 |
| JP | 2001-2555 A | 1/2001 |

OTHER PUBLICATIONS

International Search Report, mailed Apr. 23, 2013, issued in PCT/JP2013/054307.
Japanese Office Action dated Apr. 7, 2015, for Japanese Application No. 2014-510068.

* cited by examiner

*Primary Examiner* — Leszek Kiliman
(74) *Attorney, Agent, or Firm* — Birch, Stewart, Kolasch & Birch, LLP

(57) ABSTRACT

Water-absorbable silicone rubber particles which are particles of a silicone rubber, each of which has a particle diameter ranging from 0.1 to 1,000 μm and is elastic, wherein the silicone rubber is an organopolysiloxane having a polyoxyalkylene group, contains an oxyethylene unit represented by the formula —$OCH_2CH_2$— in an amount of 20 to 80 mass %, and can absorb water in an amount of 10 parts by mass or more relative to 100 parts by mass of the silicone rubber. The silicone particles according to the present invention can impart soft touch, a soft-focusing effect and the like to a make-up cosmetic such as a foundation or an antiperspirant when added to the make-up cosmetic or the antiperspirant. In addition, since the particles have high water absorption performance, the particles can absorb sweat and therefore is expected to exhibit an effect of reducing unpleasantness such as stickiness and greasiness, oiliness of the skin and make-up deterioration.

4 Claims, No Drawings

WATER-ABSORBABLE SILICONE RUBBER PARTICLES AND METHOD FOR PRODUCING SAME

TECHNICAL FIELD

This invention relates to silicone rubber particles capable of absorbing water and a method for preparing the same.

BACKGROUND ART

From the past, silicone rubber particles are used in cosmetics for the purposes of imparting a soft feeling, a soft-focus effect and the like thereto.

In antiperspirants, for example, it is a common practice to incorporate a water-absorbing polymer therein for absorbing sweat to reduce unpleasant feeling such as sticky or slippery feeling as disclosed in JP-A S54-46842 (Patent Document 1). Since not only silicone, but also rubbery materials do not absorb water, such effects are not expected at all for these materials. For example, JP-A H09-255794 (Patent Document 2) discloses a silicone rubber powder having a polyoxyalkylene group bonded to silicon atom, which is hydrophilic, but not water absorbable.

SUMMARY OF INVENTION

Technical Problem

An object of the invention, which has been made under the above-mentioned circumstances, is to provide silicone rubber particles which when incorporated in cosmetics, impart a soft feeling, soft-focus effect and the like, and have water-absorbing ability, and are thus expected to absorb sweat for reducing unpleasant feeling such as sticky or slippery feeling, and a method for preparing the same.

Solution to Problem

Making extensive investigations to attain the above object, the inventor has found that the above object is attainable by the silicone rubber particles defined below. The invention is predicated on this finding.

Specifically, the invention provides water-absorbing silicone rubber particles and a method for preparing the same, as defined below.

[1] Water-absorbing silicone rubber particles having a particle size in the range of 0.1 to 1,000 μm and elasticity, wherein the silicone rubber is an organopolysiloxane having polyoxyalkylene groups, contains 20 to 80% by mass, based on the silicone rubber, of oxyethylene units of —OCH$_2$CH$_2$—, and is capable of absorbing at least 10 parts by mass of water per 100 parts by mass of the silicone rubber.

[2] The water-absorbing silicone rubber particles of [1] wherein the polyoxyalkylene groups are a monovalent polyoxyalkylene group, attached to a silicon atom in the organopolysiloxane, having the formula (1):

$$—R^1(OCH_2CH_2)_a(OCH(CH_3)CH_2)_bOR^2 \quad (1)$$

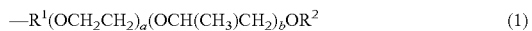

wherein $R^1$ is an alkylene group of 1 to 15 carbon atoms, $R^2$ is hydrogen, an alkyl group of 1 to 30 carbon atoms or an organic group of —(CO)—$R^3$, $R^3$ is an alkyl group of 1 to 30 carbon atoms, a is an integer of 2 to 50, and b is an integer of 0 to 15, and a divalent polyoxyalkylene group, attached to a silicon atom in the organopolysiloxane, having the formula (2):

$$—R^4(OCH_2CH_2)_c(OCH(CH_3)CH_2)_dOR^5— \quad (2)$$

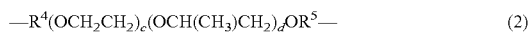

wherein $R^4$ is an alkylene group of 1 to 15 carbon atoms, $R^5$ is an alkylene group of 1 to 15 carbon atoms, c is an integer of 2 to 50, and d is an integer of 0 to 15, wherein the monovalent polyoxyalkylene group of formula (1) and the divalent polyoxyalkylene group of formula (2) are present in a mass ratio in the range from 10:90 to 95:5.

[3] The water-absorbing silicone rubber particles of [2] wherein the organopolysiloxane having polyoxyalkylene groups is obtained from addition reaction of a composition in the presence of (D) a platinum group metal based catalyst, said composition comprising (A) an organohydrogenpolysiloxane containing on average at least 3 silicon-bonded hydrogen atoms per molecule, represented by the average compositional formula (3):

$$R^6_eH_fSiO_{(4-e-f)/2} \quad (3)$$

wherein $R^6$ is a monovalent organic group of 1 to 30 carbon atoms other than an aliphatic unsaturated group, e and f are positive numbers meeting 0<e<3, 0<f≤3, and 0.1≤e+f≤3, (B) a polyoxyalkylene having a monovalent olefinic unsaturated group attached at one end, represented by the formula (4):

$$R^7(OCH_2CH_2)_a(OCH(CH_3)CH_2)_bOR^2 \quad (4)$$

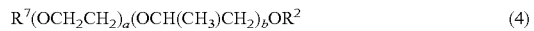

wherein $R^7$ is a monovalent olefinic unsaturated group of 2 to 15 carbon atoms, $R^2$, a and b are as defined for formula (1), and (C) a polyoxyalkylene having a monovalent olefinic unsaturated group attached at both ends, represented by the formula (5):

$$R^8(OCH_2CH_2)_c(OCH(CH_3)CH_2)_dOR^9 \quad (5)$$

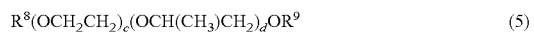

wherein $R^8$ and $R^9$ each are a monovalent olefinic unsaturated group of 2 to 15 carbon atoms, c and d are as defined for formula (2), wherein the number of monovalent olefinic unsaturated group in component (B) and monovalent olefinic unsaturated group in component (C) ranges from 0.5 to 2 per silicon-bonded hydrogen atom in component (A).

[4] The water-absorbing silicone rubber particles of any one of [1] to [3] which are of spherical shape.

[5] A method for preparing water-absorbing silicone rubber particles, comprising the steps of:

subjecting (A) an organohydrogenpolysiloxane containing on average at least 3 silicon-bonded hydrogen atoms per molecule, represented by the average compositional formula (3):

$$R^6_eH_fSiO_{(4-e-f)/2} \quad (3)$$

wherein $R^6$ is a monovalent organic group of 1 to 30 carbon atoms other than an aliphatic unsaturated group, e and f are positive numbers meeting 0<e<3, 0<f≤3, and 0.1≤e+f≤3, and (B) a polyoxyalkylene having a monovalent olefinic unsaturated group attached at one end, represented by the formula (4):

$$R^7(OCH_2CH_2)_a(OCH(CH_3)CH_2)_bOR^2 \quad (4)$$

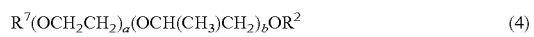

wherein $R^7$ is a monovalent olefinic unsaturated group of 2 to 15 carbon atoms, $R^2$ is hydrogen, an alkyl group of 1 to 30 carbon atoms or an organic group of —(CO)—$R^3$, $R^3$ is an alkyl group of 1 to 30 carbon atoms, a is an integer of 2 to 50, and b is an integer of 0 to 15, to addition reaction in the presence of (D) a platinum group metal based catalyst, mixing the reaction product with (C) a polyoxyalkylene having a monovalent olefinic unsaturated group attached at both ends, represented by the formula (5):

$$R^8(OCH_2CH_2)_c(OCH(CH_3)CH_2)_dOR^9 \quad (5)$$

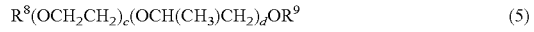

wherein $R^8$ and $R^9$ each are a monovalent olefinic unsaturated group of 2 to 15 carbon atoms, c is an integer of 2 to 50, and d is an integer of 0 to 15, dispersing the resulting dissolved liquid in (E) an insoluble liquid, and thereafter allowing addition reaction to take place under the action of the platinum group metal based catalyst (D), for curing into a rubber state.

Advantageous Effects of Invention

The silicone particles according to the invention can impart a soft feeling, soft-focus effect and the like when added to make-up cosmetics such as foundation or antiperspirant agents. In addition, because of their water-absorbing capacity, the particles are expected to exert an effect of absorbing sweat for reducing unpleasant feelings such as sticky and slippery feelings and suppressing shininess and make-up deterioration.

DESCRIPTION OF EMBODIMENTS

A first embodiment of the invention provides water-absorbing silicone rubber particles having a particle size in the range of 0.1 to 1,000 μm, wherein the silicone rubber is an organopolysiloxane having polyoxyalkylene groups, contains 20 to 80% by mass, based on the silicone rubber, of oxyethylene units of $-OCH_2CH_2-$, and is capable of absorbing at least 10 parts by mass of water per 100 parts by mass of the silicone rubber.

A second embodiment of the invention provides a method for preparing spherical water-absorbing silicone rubber particles, characterized by dispersing a silicone rubber precursor composition in an insoluble liquid, and then curing the composition into a rubber state.

Now the invention is described in further detail.

[Water-Absorbing Silicone Rubber Particles]

The water-absorbing silicone rubber particles according to the invention have a particle size in the range of 0.1 to 1,000 μm, preferably 0.5 to 600 μm. If particles with a size of less than 0.1 μm are present, such particles are so agglomerative that they may not be readily dispersed to primary particles. If particles with a size of more than 1,000 μm are present, they may cause cosmetic materials to lose smoothness and exhibit a rough feeling. Notably, the particle size is measurable by any microscopic methods. In this context, it is preferred that sample particles be dispersed on a sample plate without overlapping. For example, sample particles may be spread on the sample plate in a rubbing manner, using a rod with a flat or spherical tip.

Upon observation under an optical microscope, particle size can be measured even in a liquid dispersed state. For example, a liquid dispersion sandwiched between a slide glass and a cover glass is observed. If sample particles overlap each other, the dispersion may be further diluted with the liquid.

With respect to the number of particles measured and the site of measurement, more is desirable because reliability becomes higher. It suffices at minimum that the number of particles measured is 50 and the site of measurement is 1.

The shape of water-absorbing silicone rubber particles is not particularly limited and may be selected from spherical, spindle, flat and irregular shapes, for example, with the spherical shape being preferred. As used herein, the "spherical" particles include not only particles of true sphere, but also deformed spheres having on average an aspect ratio (length of longest axis to length of shortest axis) in the range of 1 to 4, preferably from 1 to 2, more preferably from 1 to 1.6, and even more preferably from 1 to 1.4. The shape of particles may be confirmed by observing them under an optical microscope or electron microscope.

The water-absorbing silicone rubber particles are constructed of silicone rubber which is elastic and tack-free. The silicone rubber preferably has a rubber hardness in the range of 10 to 95, more preferably 20 to 85, as measured by an Asker C durometer prescribed in the Society of Rubber Industry, Japan standard (SRIS), 0101. With a rubber hardness of less than 10, such particles are so agglomerative that they may not be readily dispersed to primary particles. With a rubber hardness of more than 95, soft feeling may become short.

The silicone rubber is capable of absorbing at least 10 parts, preferably at least 30 parts, and more preferably at least 50 parts by mass of water per 100 parts by mass of the silicone rubber. If the water absorption capacity is less than 10 parts by mass, it is estimated that silicone rubber particles become less effective for reducing unpleasant feelings such as sticky and slippery feelings and suppressing shininess and make-up deterioration. Understandably, since more water absorption is preferable, the upper limit of water absorption is not particularly limited. In a practical sense, the water absorption may be up to 1,000 parts, especially up to 500 parts by mass, for example.

The silicone rubber is an organopolysiloxane having polyoxyalkylene groups, and contains 20 to 80%, preferably 25 to 75%, and more preferably 30 to 70% by mass of oxyethylene units represented by the formula $-OCH_2CH_2-$, based on the organopolysiloxane having polyoxyalkylene groups. If the oxyethylene content is less than 20% by mass, the water absorption may become smaller. If the oxyethylene content exceeds 80% by mass, the rubber hardness may become higher.

Preferably the polyoxyalkylene groups are a monovalent polyoxyalkylene group, attached to a silicon atom in the organopolysiloxane, having the formula (1):

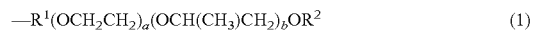

$-R^1(OCH_2CH_2)_a(OCH(CH_3)CH_2)_bOR^2$     (1)

wherein $R^1$ is an alkylene group of 1 to 15 carbon atoms, $R^2$ is hydrogen, an alkyl group of 1 to 30 carbon atoms or an organic group of $-(CO)-R^3$, $R^3$ is an alkyl group of 1 to 30 carbon atoms, a is an integer of 2 to 50, and b is an integer of 0 to 15, and a divalent polyoxyalkylene group, attached to a silicon atom in the organopolysiloxane, having the formula (2):

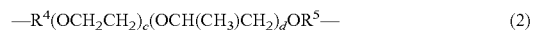

$-R^4(OCH_2CH_2)_c(OCH(CH_3)CH_2)_dOR^5-$     (2)

wherein $R^4$ is an alkylene group of 1 to 15 carbon atoms, $R^5$ is an alkylene group of 1 to 15 carbon atoms, c is an integer of 2 to 50, and d is an integer of 0 to 15.

Exemplary groups of $R^1$ include ethylene, propylene, butylene, pentylene, hexylene, heptylene, octylene, decylene, dodecylene, and pentadecylene, with alkylene groups of 3 to 5 carbon atoms being preferred. Examples of the alkyl group of 1 to 30 carbon atoms, represented by $R^2$, include methyl, ethyl, propyl, butyl, pentyl, hexyl, heptyl, octyl, decyl, undecyl, dodecyl, tetradecyl, pentadecyl, hexadecyl, heptadecyl, octadecyl, nonadecyl, eicosyl, heneicosyl, docosyl, tricosyl, tetracosyl, and triacontyl. Exemplary groups of $R^3$ include the same as exemplified for $R^2$. Preferably $R^2$ is hydrogen or an alkyl group of 1 to 5 carbon atoms. The subscript a is preferably an integer of 4 to 25, and b is preferably an integer of 0 to 5. Exemplary groups of $R^4$ include the same as exemplified for $R^1$, with alkylene groups of 3 to 5 carbon atoms being preferred. Exemplary groups of $R^5$ include the same as exemplified for $R^1$, with alkylene groups of 3 to 5 carbon atoms being preferred. The subscript c is preferably an integer of 4 to 25, and d is preferably an integer of 0 to 5.

Since the divalent polyoxyalkylene group of formula (2) is attached to a silicon atom in the organopolysiloxane, the organopolysiloxane has a crosslinked structure, which leads to a rubber elastomer. As the proportion of divalent polyoxyalkylene group of formula (2) in the polyoxyalkylene groups increases, the crosslinking density increases and the water absorption decreases. As the proportion of monovalent polyoxyalkylene group of formula (1) in the polyoxyalkylene groups increases, the crosslinking density decreases and the rubber decreases in hardness or becomes sticky.

Preferably the monovalent polyoxyalkylene group of formula (1) and the divalent polyoxyalkylene group of formula (2) are present in a mass ratio in the range from 10:90 to 95:5, more preferably from 20:80 to 90:10, and even more preferably from 30:70 to 85:15.

The organopolysiloxane having polyoxyalkylene groups is not limited with respect to the raw materials from which the polyoxyalkylene groups and the organopolysiloxane are derived, and the reaction method for preparing the same. That is, the reaction method of bonding polyoxyalkylene groups and the reaction method of preparing a rubber elastomer are not limited. Preferably, the organopolysiloxane having polyoxyalkylene groups is obtained from addition reaction of a composition in the presence of (D) a platinum group metal based catalyst, the composition comprising (A) an organohydrogenpolysiloxane containing on average at least 3 silicon-bonded hydrogen atoms per molecule, represented by the average compositional formula (3):

$$R^6_e H_f SiO_{(4-e-f)/2} \quad (3)$$

wherein $R^6$ is a monovalent organic group of 1 to 30 carbon atoms other than an aliphatic unsaturated group, e and f are positive numbers meeting $0<e<3$, $0<f\leq3$, and $0.1\leq e+f\leq3$, (B) a polyoxyalkylene having a monovalent olefinic unsaturated group attached at one end, represented by the formula (4):

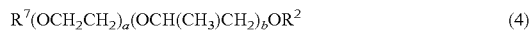

$$R^7(OCH_2CH_2)_a(OCH(CH_3)CH_2)_bOR^2 \quad (4)$$

wherein $R^7$ is a monovalent olefinic unsaturated group of 2 to 15 carbon atoms, $R^2$, a and b are as defined for formula (1), and (C) a polyoxyalkylene having a monovalent olefinic unsaturated group attached at both ends, represented by the formula (5):

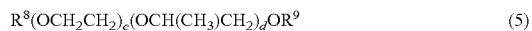

$$R^8(OCH_2CH_2)_c(OCH(CH_3)CH_2)_dOR^9 \quad (5)$$

wherein $R^8$ and $R^9$ each are a monovalent olefinic unsaturated group of 2 to 15 carbon atoms, c and d are as defined for formula (2), wherein the number of monovalent olefinic unsaturated group in component (B) and monovalent olefinic unsaturated group in component (C) ranges from 0.5 to 2 per silicon-bonded hydrogen atom in component (A).

Component (C) functions to crosslink component (A) so that the structure may become a rubber elastomer. While an organopolysiloxane having at least 2 monovalent olefinic unsaturated groups per molecule and an organic compound (exclusive of component (C)) may be compounded as the crosslinking component, it is preferred to minimize their amount because they act to reduce the water absorption capacity.

Component (A) is an organohydrogenpolysiloxane. In formula (3) representative of the organohydrogenpolysiloxane, $R^6$ preferably has 1 to 20 carbon atoms, more preferably 1 to 6 carbon atoms. Exemplary groups of $R^6$ include alkyl groups such as methyl, ethyl, propyl, butyl, pentyl, hexyl, heptyl, octyl, decyl, undecyl, dodecyl, tetradecyl, pentadecyl, hexadecyl, heptadecyl, octadecyl, nonadecyl, eicosyl, heneicosyl, docosyl, tricosyl, tetracosyl, and triacontyl; aryl groups such as phenyl, tolyl and naphthyl; aralkyl groups such as benzyl and phenethyl; cycloalkyl groups such as cyclopentyl, cyclohexyl and cycloheptyl; and monovalent organic groups in which some or all carbon-bonded hydrogen atoms in the foregoing groups are substituted by atoms, typically halogen atoms (e.g., fluorine, chlorine, bromine and iodine atoms) and/or substituent groups such as acryloyloxy, methacryloyloxy, epoxy, glycidoxy, carboxyl, polypropylene, and polyglycerol. In formula (3), e and f are preferably positive numbers meeting the range: $0<e\leq2.295$, $0.005\leq f\leq2.3$, and $0.5\leq e+f\leq2.3$.

The organohydrogenpolysiloxane as component (A) is constructed by siloxane units which include $R^6_2SiO_{2/2}$, $R^6HSiO_{2/2}$, $H_2SiO_{2/2}$, $R^6SiO_{3/2}$, $HSiO_{3/2}$, and $SiO_{4/2}$ units as molecule non-terminal units, and $R^6_3SiO_{1/2}$, $R^6_2HSiO_{1/2}$, $R^6H_2SiO_{1/2}$, and $H_3SiO_{1/2}$ units as molecule terminal units.

The organohydrogenpolysiloxane as component (A) should contain on average at least 3 silicon-bonded hydrogen atoms (SiH groups) per molecule, preferably at least 4 SiH groups. If the number of silicon-bonded hydrogen atoms per molecule is less than the range, the rubber may have low hardness or become sticky. Although the upper limit of SiH group count is not critical, the SiH group count is preferably such that SiH-containing units may account for up to 80 mol %, especially up to 60 mol % of the molecule.

The organohydrogenpolysiloxane as component (A) may have a linear, cyclic or branched structure, with the linear or branched structure being preferred.

The organohydrogenpolysiloxane as component (A) should preferably have a viscosity at 25° C. of up to 100,000 mm²/s, more preferably up to 10,000 mm²/s. As long as the viscosity is up to 100,000 mm²/s, dispersion in a dispersing medium becomes quite easy in the preparation method to be described later. Although the lower limit of viscosity is not critical, the viscosity may be, in a practical sense, at least 0.4 mm²/s, especially at least 2 mm²/s, for example. Notably, the viscosity is measurable by an Ostwald viscometer.

Component (B) is a polyoxyalkylene having a monovalent olefinic unsaturated group attached at one end. In formula (4) representative of this polyoxyalkylene, exemplary groups of $R^7$ include vinyl, allyl, propenyl, butenyl, pentenyl, hexenyl, heptenyl, octenyl, decenyl, dodecenyl, and pentadecenyl, with the monovalent olefinic unsaturated groups of 3 to 5 carbon atoms being preferred.

Preferably, the polyoxyalkylene having a monovalent olefinic unsaturated group attached at one end as component (B) is water soluble. If it is water insoluble, the resulting silicone rubber has a reduced water absorption capacity.

Component (C) is a polyoxyalkylene having a monovalent olefinic unsaturated group attached at both ends. In formula (5) representative of the polyoxyalkylene, exemplary groups of $R^8$ and $R^9$ include the same as exemplified for $R^7$, with the monovalent olefinic unsaturated groups of 3 to 5 carbon atoms being preferred.

Preferably, the polyoxyalkylene having a monovalent olefinic unsaturated group attached at both ends as component (C) is water soluble. If it is water insoluble, the resulting silicone rubber has a reduced water absorption capacity.

As alluded to previously, components (A), (B) and (C) should be present in such amounts that the number of monovalent olefinic unsaturated group in component (B) and monovalent olefinic unsaturated group in component (C) ranges from 0.5 to 2 per silicon-bonded hydrogen atom in component (A). Preferably the ratio ranges from 0.7 to 1.5. If the composition is such that the ratio is less than 0.5 or more than 2, then the resulting rubber is likely to become sticky and extraordinarily reactive.

The amounts of components (B) and (C) relative to component (A) must be adjusted such that the oxyethylene units of the formula: —OCH$_2$CH$_2$— account for 20 to 80%, preferably 25 to 75%, and more preferably 30 to 70% by mass of the silicone rubber having polyoxyalkylene groups.

Furthermore, the proportion of components (B) and (C) should preferably be adjusted so as to meet the above-specified ratio of the monovalent polyoxyalkylene group of formula (1) to the divalent polyoxyalkylene group of formula (2).

Component (D) is a platinum group metal based catalyst, which serves to promote addition reaction of SiH groups in component (A) to monovalent olefinic unsaturated groups in components (B) and (C). As component (D), the catalysts may be used alone or in admixture of two or more.

Included in component (D) are well-known catalysts used in hydrosilylation reaction. Specifically, platinum group metal based catalysts are useful. Exemplary catalysts include platinum group metals alone such as platinum (inclusive of platinum black), rhodium and palladium; platinum chloride, chloroplatinic acid, and chloroplatinic acid salts such as H$_2$PtCl$_4$.kH$_2$O, H$_2$PtCl$_6$.kH$_2$O, NaHPtCl$_6$.kH$_2$O, KHPtCl$_6$.kH$_2$O, Na$_2$PtCl$_6$.kH$_2$O, K$_2$PtCl$_4$.kH$_2$O, PtCl$_4$.kH$_2$O, PtCl$_2$, and Na$_2$HPtCl$_4$-kH$_2$O wherein k is an integer of 0 to 6; alcohol-modified chloroplatinic acid (see U.S. Pat. No. 3,220,972); complexes of chloroplatinic acid with olefins (see U.S. Pat. No. 3,159,601, U.S. Pat. No. 3,159,662, U.S. Pat. No. 3,775,452); platinum group metals such as platinum black and palladium on carriers such as alumina, silica, and carbon; rhodium-olefin complexes; chlorotris(triphenylphosphine)rhodium (Wilkinson catalyst); and complexes of platinum chloride, chloroplatinic acid or chloroplatinic acid salts with vinyl-containing siloxanes.

The amount of component (D) blended may be an effective amount as the hydrosilylation reaction catalyst. Specifically, the amount of platinum group metal in component (D) relative to the total amount of components (A), (B) and (C), calculated on a mass basis, is typically about 0.1 to 500 ppm, preferably about 0.5 to 200 ppm, and more preferably about 1 to 100 ppm.

[Method for Preparing Water-Absorbing Silicone Rubber Particles]

The water-absorbing silicone rubber particles of the invention may be prepared, for example, by grinding a silicone rubber formed of an organopolysiloxane having polyoxyalkylene groups. With this method, particles of irregular shape are obtained. Examples of the grinding machine include ball mills, media-agitating mills, roller mills, hammer mills, and jet mills. Where heat is generated during grinding, the operation may be done while cooling with water, liquefied nitrogen or the like. If grinding is difficult because of rubber elasticity, the rubber is cooled with liquefied nitrogen or the like so that rubber elasticity is mitigated or eliminated, after which the rubber in hard state may be ground.

In the preferred method, the water-absorbing silicone rubber particles of the invention is prepared by dispersing a precursor composition for the silicone rubber in (E) an insoluble liquid and thereafter curing into a rubber state. With this method, particles of spherical shape are obtainable.

The liquid as component (E) is a dispersing medium in which the precursor composition for the silicone rubber is dispersed. The liquid is not particularly limited as long as the precursor composition for the silicone rubber is insoluble therein. Exemplary liquids include naturally occurring animal and vegetable oils and fats, semi-synthetic oils and fats, hydrocarbon oils, higher alcohols, ethers, ester oils, glyceride oils, fluorinated fluids, and silicone oils. Since the silicone rubber particles of the invention are water absorbable, it is believed that all or some of the components of the precursor composition dissolve in water. Therefore, water cannot be used as component (E).

Where component (E) has a high melting point, dispersion of the precursor composition for the silicone rubber and curing reaction into rubber may be carried out at a temperature above the melting point.

Examples of natural animal and vegetable oils and fats, semi-synthetic oils and fats include avocado oil, linseed oil, almond oil, insect wax, perilla oil, olive oil, cacao fat, kapok wax, kaya oil, carnauba wax, liver oil, candelilla wax, purified candelilla wax, beef tallow, beef foot oil, beef bone fat, hardened beef tallow, apricot kernel oil, spermaceti, hydrogenated oil, wheat germ oil, sesame oil, rice germ oil, rice bran oil, sugar cane wax, sasanqua oil, safflower oil, shea butter, tung oil, cinnamon oil, jojoba oil, squalane, squalene, shellac wax, turtle oil, soybean oil, tea seed oil, tsubaki oil, primrose oil, corn jerm oil, lard, canola oil, Japanese tung oil, rice bran wax, germ oil, horse oil, persic oil, palm oil, palm kernel oil, castor oil, hardened castor oil, castor oil fatty acid methyl ester, sunflower oil, grape seed oil, bayberry wax, jojoba oil, macadamia nut oil, bees wax, mink oil, meadowfoam oil, cotton seed oil, cotton wax, Japan haze wax, Japan haze kernel oil, montan wax, coconut oil, hardened coconut oil, tri(coconut oil fatty acid) glyceride, mutton tallow, peanut oil, lanolin, liquid lanolin, reduced lanolin, lanolin alcohol, hard lanolin, acetic acid lanolin, acetic acid lanolin alcohol, lanolin fatty acid isopropyl, polyoxyethylene lanolin alcohol ester, polyoxyethylene lanolin alcohol acetate, lanolin fatty acid polyethylene glycol, polyoxyethylene hydrogenated lanolin alcohol ether, and egg oil.

Suitable hydrocarbon oils include linear or branched hydrocarbon oils which may be either volatile or non-volatile. Examples of the hydrocarbon oils include synthetic squalane, vegetable squalane, squalene, liquid isoparaffin, light isoparaffin, hydrogenated polyisobutene, isododecane, light liquid isoparaffin, isohexadecane, liquid paraffin, pristane, α-olefin oligomers, ozokerite, ceresin, paraffin, paraffin wax, polyethylene wax, polyethylene-polypropylene wax, ethylene/propylene/styrene copolymers, butylene/propylene/styrene copolymers, polyisobutylene, microcrystalline wax, vaseline, etc.

Suitable higher alcohols are, for example, alcohols of preferably at least 6 carbon atoms, more preferably 10 to 30 carbon atoms. Exemplary higher alcohols include lauryl alcohol, myristyl alcohol, palmityl alcohol, stearyl alcohol, behenyl alcohol, hexadecyl alcohol, oleyl alcohol, isostearyl alcohol, hexyl dodecanol, octyl dodecanol, cetostearyl alcohol, 2-decyltetradecinol, cholesterol, phytosterol, polyoxyethylene cholesterol ether, monostearyl glycerol ether (batyl alcohol), monooleyl glyceryl ether (selachyl alcohol), etc.

Exemplary ether fluids include mono- or di-alkyl ethers of ethylene glycol, diethylene glycol or triethylene glycol; mono- or di-alkyl ethers of butylene glycol, propylene glycol, dipropylene glycol, pentylene glycol or caprylyl glycol; mono-, di- or tri-alkyl ethers of glycerol; alkyl ethers of isononyl alcohol, caprylyl alcohol or stearyl alcohol, etc.

Exemplary ester fluids include dioctyl succinate, diisobutyl adipate, dioctyl adipate, di(2-heptylundecyl)adipate, diisopropyl sebacate, dioctyl sebacate, dibutyloctyl sebacate, diisostearyl malate, triethyl citrate, ethylene glycol dioctanoate, neopentyl glycol dioctanoate, propylene glycol dicaprylate, neopentyl glycol dicaprylate, trimethylol propane trioctanoate, trimethylol propane triisostearate, pentaerythritol tetraoleate, ethyl acetate, butyl acetate, amyl acetate, octyldodecyl neopentanoate, cetyl octanoate, isononyl isononanoate, isotridecyl isononanoate, hexyldecyl dimethyloctanoate, ethyl laurate, hexyl laurate, isopropyl myristate, myristyl myristate, isocetyl myristate, octyldodecyl myristate, isopropyl palmitate, octyl palmitate, cetyl palmitate, isocetyl palmitate, isostearyl palmitate, butyl stearate, hexyldecyl stearate, isopropyl isostearate, isocetyl isostearate, decyl oleate, oleyl oleate, octyldodecyl oleate, ethyl linolate, isopropyl linolate, cetyl lactate, myristyl lactate, cholesteryl hydroxystearate, dioctyldodecyl lauroylglutamate, lauroylsarcosine isopropyl, octyldodecyl gum ester, etc.

Exemplary glyceride fluids include acetoglyceryl, glyceryl triisooctanoate, glyceryl trimyristate, glyceryl triisopalmitate, glyceryl triisostearate, glyceryl tribehenate, glyceryl diisostearate, glyceryl monostearate, diglyceryl isostearate/myristate, and dipentaerythritol fatty acid esters.

Exemplary fluorinated fluids include perfluoropolyether, perfluorodecalin, and perfluorooctane.

Exemplary silicone fluids include low to high viscosity, linear or branched organopolysiloxanes such as dimethylpolysiloxane, tristrimethylsiloxymethylsilane, caprylyl methicone, phenyl trimethicone, tetrakistrimethylsiloxysilane, methylphenylpolysiloxane, methylhexylpolysiloxane, methylhydrogenpolysiloxane, and dimethylsiloxane-methylphenylsiloxane copolymers; cyclic organopolysiloxanes such as octamethylcyclotetrasiloxane, decamethylcyclopentasiloxane, dodecamethylcyclohexasiloxane, tetramethyltetrahydrogencyclotetrasiloxane, and tetramethyltetraphenylcyclotetrasiloxane; amino-modified organopolysiloxane; pyrrolidone-modified organopolysiloxane; pyrrolidone carboxylic acid-modified organopolysiloxane; higher alkoxy-modified silicones such as stearoxysilicone; higher fatty acid-modified silicones, alkyl-modified silicones; long chain alkyl-modified silicones; amino acid-modified silicones; fluorine-modified silicones, etc.

As alluded to previously, the precursor composition for silicone rubber to be dispersed in the insoluble liquid as component (E) preferably comprises the organohydrogenpolysiloxane as component (A), the polyoxyalkylene having a monovalent olefinic unsaturated group attached at one end as component (B), the polyoxyalkylene having a monovalent olefinic unsaturated group attached at both ends as component (C), and the platinum group metal based catalyst as component (D).

Further preferably, the water-absorbing silicone rubber particles are prepared by a method comprising the steps of subjecting the organohydrogenpolysiloxane as component (A) and the polyoxyalkylene having a monovalent olefinic unsaturated group attached at one end as component (B) to addition reaction in the presence of the platinum group metal based catalyst as component (D), mixing the reaction product with the polyoxyalkylene having a monovalent olefinic unsaturated group attached at both ends as component (C), dispersing the resulting dissolved liquid in the insoluble liquid as component (E), and thereafter allowing addition reaction to take place under the action of the platinum group metal based catalyst (D), for curing into a rubber state.

In this embodiment, when components (A) and (B) are reacted, they are preferably used in such amounts that 0.10 to 0.95 mole, more preferably 0.20 to 0.90 mole of olefinic unsaturated groups in component (B) may be available per mole of SiH groups in component (A). Thereafter, olefinic unsaturated groups in component (C) are reacted with the residual SiH groups in component (A). At this point, components (B) and (C) are preferably used such that the resulting organopolysiloxane may contain the monovalent polyoxyalkylene group of formula (1) and the divalent polyoxyalkylene group of formula (2) in a mass ratio of 10:90 to 95:5, more preferably 20:80 to 90:10, and even more preferably 30:70.

The addition reaction between components (A) and (B) may be carried out in an organic solvent. Examples of the organic solvent include lower alcohols of up to 5 carbon atoms, such as methanol, ethanol, 2-propanol, and butanol; aromatic hydrocarbons such as toluene and xylene; aliphatic or alicyclic hydrocarbons such as n-pentane, n-hexane, and cyclohexane; and halogenated hydrocarbons such as dichloromethane, chloroform and carbon tetrachloride. Inter alia, ethanol and 2-propanol are preferred particularly in cosmetic application. Although the addition reaction conditions are not particularly limited, the reaction is preferably carried out under reflux for 1 to 20 hours.

When an organic solvent is used for the addition reaction between components (A) and (B), the organic solvent is distilled off. Understandably, if the organic solvent is insoluble in component (E), it may not be distilled off or may be partially distilled off. Distillation of the organic solvent may be carried out under atmospheric pressure or reduced pressure, while the temperature is preferably up to 120° C. For efficient distillation at such a temperature, the preferred setting is a reduced pressure, or in a stream of inert gas if the pressure is atmospheric.

After the addition reaction between components (A) and (B), the reaction product is mixed with the polyoxyalkylene having a monovalent olefinic unsaturated group attached at both ends as component (C) and dissolved therein. If the reaction product of components (A) and (B) or component (C) has a high melting point, their mixing and dissolution may be carried out at a temperature above the melting point. If the addition reaction product of components (A) and (B) and component (C) do not dissolve into a clear solution, a dissolvable composition must be established by suitable means such as by increasing the proportion of component (B) relative to component (A).

A suitable dispersing machine may be used when the dissolved mixture of the addition reaction product of components (A) and (B) and component (C) is dispersed in the insoluble liquid as component (E). Suitable machines include general agitating machines such as propeller blades, turbine blades or paddle blades; high-speed rotation centrifugal agitating machines such as homo-disper; high-speed rotation shear agitating machines such as homo-mixer, Ultra-Turrax®, and Emulder®; high-speed rotation gap passage emulsifying/dispersing machines such as colloid mill; high-pressure injection emulsifying/dispersing machines such as high-pressure homogenizer, Nanomizer®, micro-fluidizer, Star Burst®; and membrane emulsifying machines such as ultrasonic emulsifier, SPG membrane emulsifier and micro-channel emulsifier.

When the dissolved mixture of the addition reaction product of components (A) and (B) and component (C) is dispersed in component (E), it is acceptable to blend and dissolve an organic solvent which is insoluble in water and component (E), in the dissolved mixture of the addition reaction product of components (A) and (B) and component (C).

Although the addition reaction conditions for the dissolved mixture of the addition reaction product of components (A) and (B) and component (C) are not particularly limited, reaction at 50 to 120° C. for 1 to 20 hours is preferred. While addition reaction takes place under the action of the platinum group metal based catalyst as component (D) previously used in the addition reaction of component (A) to component (B), extra component (D) may be added.

At the end of addition reaction, component (E) is removed from the resulting particle dispersion, yielding water-absorbing silicone rubber particles according to the invention. In this case, the particles thus obtained are typically spherical. If component (E) is volatile, it may be removed by heating under atmospheric pressure or reduced pressure. Specifically, component (E) is removed by suitable means, for example, by keeping the liquid dispersion stationary under heating, by agitating and fluidizing the liquid dispersion under heating, by spraying and dispersing the liquid dispersion in a hot air stream such as a spray drier, or by utilizing a flow of heat medium. It is noted that as treatment prior to the removal, the liquid dispersion may be concentrated by such means as filtration/separation, centrifugal separation or decantation. If component (E) is non-volatile, component (E) is washed with a volatile liquid which can dissolve component (E), before the volatile liquid is removed by the means described just above. Specifically, washing is carried out by adding a wash liquid, agitating mixing and thereafter, concentrating by the means described just above. By repeating this operation, the content of component (E) can be reduced. Suitable wash liquids include volatile liquids among component (E) and the organic solvents used in the addition reaction between components (A) and (B).

Washing operation may be carried out prior to or subsequent to the removal of component (E), for the purposes of removing unreacted components (A), (B) and (C), and removing component (D). The washing operation and removal of wash liquid may be carried out as mentioned above. The wash liquid used herein is preferably the organic solvent used in the addition reaction between components (A) and (B) or water.

When particles left after the removal of component (E) and wash liquid are agglomerated together, such agglomerates may be disintegrated by the above-mentioned grinding machine.

EXAMPLES

Examples and Comparative Examples are given below for further illustrating the invention, but the invention is not limited to the Examples.

Example 1

A glass flask of volume 500 ml equipped with a reflux condenser and anchor-shaped impeller agitator was charged with 44.5 g of methylhydrogenpolysiloxane having a viscosity of 106 mm$^2$/s, represented by the average formula (6), 23.8 g of polyoxyethylene having allyl attached at one end, represented by the average formula (7), 57.6 g of polyoxyethylene having allyl attached at one end, represented by the average formula (8), 150 g of isopropyl alcohol, and 0.08 g of an ethanol solution of a complex of chloroplatinic acid with vinyl-containing siloxane (platinum content 3% by mass), after which addition reaction was carried out at 80° C. for 8 hours. The reaction mixture was transferred to an eggplant shaped glass flask of volume 500 ml. Using a rotary evaporator, isopropyl alcohol was distilled off at 70° C. under reduced pressure. A glass flask of volume 500 ml equipped with an anchor-shaped impeller agitator was charged with the addition reaction product of methylhydrogenpolysiloxane and polyoxyethylenes having allyl at one end, and 24.1 g of polyoxyethylene having allyl attached at both ends, represented by the average formula (9). The contents were mixed and dissolved by agitating at 40° C. At this point, the number of allyl groups in the polyoxyethylene having allyl attached at one end and allyl groups in the polyoxyethylenes having allyl attached at both ends is 0.87 per silicon-bonded hydrogen atom in the methylhydrogenpolysiloxane. Also the silicone rubber at the end of addition reaction contains 65% by mass of oxyethylene units. Further, the proportion of monovalent polyoxyalkylene groups to divalent polyoxyalkylene groups at the end of addition reaction is 77:23 in mass ratio. With stirring at 40° C. by a homo-mixer, the thus dissolved liquid was slowly added to a glass flask of volume 500 ml equipped with an anchor-shaped impeller agitator and charged with 150 g of dimethylpolysiloxane having a viscosity of 10 mm$^2$/s. The resulting liquid dispersion in dimethylpolysiloxane as dispersing medium was kept at 80° C. for 8 hours for addition reaction to take place.

The dispersion was combined with 150 g of decamethylcyclopentasiloxane, agitated, and filtered through a paper filter in a pressure filtration unit. The same operation was repeated two more times for removing dimethylpolysiloxane. Next, the dispersion was combined with 150 g of ion-exchanged water, agitated, and filtered through a paper filter in a pressure filtration unit. The same operation was repeated two more times for washing with ion-exchanged water. The dewatered product was transferred to a stainless steel tray and dried at a temperature of 105° C. in a hot-air circulating drier, yielding silicone rubber particles.

On observation under an electron microscope, the silicone rubber particles thus obtained were spherical particles having a particle size of 20 to 530 μm. The silicone rubber particles were added to water. On observation under an optical microscope after 1 hour, it was found that the particles swelled due to water absorption and enlarged as a whole, with a maximum particle size of 800 μm being recorded.

Separately, a dissolved liquid containing the addition reaction product of methylhydrogenpolysiloxane and polyoxyethylenes having allyl attached at one end and polyoxyethylene having allyl attached at both ends was prepared by the same procedure as above. The dissolved liquid was cast into an aluminum dish so as to reach a thickness of 10 mm, and heated in a thermostat chamber at 80° C. for 8 hours, yielding a tack-free silicone rubber. The silicone rubber had a hardness of 41 as measured by an Asker C durometer prescribed in the Society of Rubber Industry, Japan standard (SRIS), 0101. A piece of about 1 g was cut out of the silicone rubber. After the mass of this rubber piece was measured, it was immersed in water for 15 hours. In the course, the silicone rubber piece enlarged in size, indicating a swell due to water absorption. The silicone rubber piece was taken out of water, wiped dry with tissue paper, and measured for its mass. A water absorption capacity was computed to be 2.6 g per gram of the silicone rubber piece.

[Chemical Formula 1]

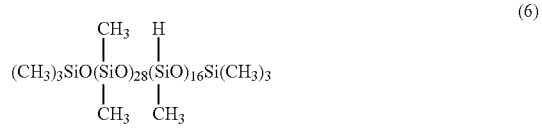

Example 2

A glass flask of volume 500 ml equipped with a reflux condenser and anchor-shaped impeller agitator was charged with 48.2 g of methylhydrogenpolysiloxane having a viscosity of 27 mm²/s, represented by the average formula (10), 66.7 g of polyoxyethylene having allyl attached at one end, represented by the average formula (8), 150 g of isopropyl alcohol, and 0.08 g of an ethanol solution of a complex of chloroplatinic acid with vinyl-containing siloxane (platinum content 3% by mass), after which addition reaction was carried out at 80° C. for 4 hours. The reaction mixture was transferred to an eggplant shaped glass flask of volume 500 ml. Using a rotary evaporator, isopropyl alcohol was distilled off at 70° C. under reduced pressure. A glass flask of volume 500 ml equipped with an anchor-shaped impeller agitator was charged with the addition reaction product of methylhydrogenpolysiloxane and polyoxyethylene having allyl attached at one end, and 35.1 g of polyoxyethylene having allyl attached at both ends, represented by the average formula (9). The contents were mixed and dissolved by agitating at 40° C. At this point, the number of allyl groups in the polyoxyethylene having allyl attached at one end and allyl groups in the polyoxyethylenes having allyl attached at both ends is 0.87 per silicon-bonded hydrogen atom in the methylhydrogenpolysiloxane. Also the silicone rubber at the end of addition reaction contains 63% by mass of oxyethylene units. Further, the proportion of monovalent polyoxyalkylene groups to divalent polyoxyalkylene groups at the end of addition reaction is 65:35 in mass ratio. With stirring at 40° C., the thus dissolved liquid was slowly added to a glass flask of volume 500 ml equipped with an anchor-shaped impeller agitator and charged with 150 g of dimethylpolysiloxane having a viscosity of 10 mm²/s. The resulting liquid dispersion in dimethylpolysiloxane as dispersing medium was kept at 80° C. for 4 hours for addition reaction to take place.

The dispersion was combined with 150 g of decamethylcyclopentasiloxane, agitated, and filtered through a paper filter in a pressure filtration unit. The same operation was repeated two more times for removing dimethylpolysiloxane. Next, the dispersion was combined with 150 g of ion-exchanged water, agitated, and filtered through a paper filter in a pressure filtration unit. The same operation was repeated two more times for washing with ion-exchanged water. The dewatered product was transferred to a stainless steel tray and dried at a temperature of 105° C. in a hot-air circulating drier, yielding silicone rubber particles.

On observation under an electron microscope, the silicone rubber particles thus obtained were spherical particles having a particle size of 30 to 220 μm. The silicone rubber particles were added to water. On observation under an optical microscope after 1 hour, it was found that the particles swelled due to water absorption and enlarged as a whole, with a maximum particle size of 300 μm being recorded.

Separately, a dissolved liquid containing the addition reaction product of methylhydrogenpolysiloxane and polyoxyethylene having allyl attached at one end and polyoxyethylene having allyl attached at both ends was prepared by the same procedure as above. The dissolved liquid was cast into an aluminum dish so as to reach a thickness of 10 mm, and heated in a thermostat chamber at 80° C. for 4 hours, yielding a tack-free silicone rubber. The silicone rubber had a hardness of 27 as measured by an Asker C durometer prescribed in the Society of Rubber Industry, Japan standard (SRIS), 0101. A piece of about 1 g was cut out of the silicone rubber. After the mass of this rubber piece was measured, it was immersed in water for 15 hours. In the course, the silicone rubber piece enlarged in size, indicating a swell due to water absorption. The silicone rubber piece was taken out of water, wiped dry with tissue paper, and measured for its mass. A water absorption capacity was computed to be 1.5 g per gram of the silicone rubber piece.

[Chemical Formula 2]

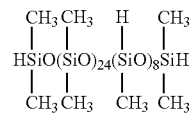

(10)

Comparative Example 1

A glass flask of volume 500 ml equipped with a reflux condenser and anchor-shaped impeller agitator was charged with 75.0 g of methylhydrogenpolysiloxane having a viscosity of 33 mm²/s, represented by the average formula (11), 44.4 g of polyoxyethylene having allyl attached at one end, represented by the average formula (12), 150 g of isopropyl alcohol, and 0.07 g of an ethanol solution of a complex of chloroplatinic acid with vinyl-containing siloxane (platinum content 3% by mass), after which addition reaction was carried out at 80° C. for 3 hours. The reaction mixture was transferred to an eggplant shaped glass flask of volume 500 ml. Using a rotary evaporator, isopropyl alcohol was distilled off at 70° C. under reduced pressure. A portion of 4.0 g was taken out of the addition reaction product of methylhydrogenpolysiloxane and polyoxyethylene having allyl attached at one end and fed to a glass beaker of volume 200 ml, which was further charged with 100.0 g of methylvinylpolysiloxane having a viscosity of 103 mm²/s, represented by the average formula (13) and 8.5 g of methylhydrogenpolysiloxane having a viscosity of 106 mm²/s, represented by the average formula (6). With a glass rod, the contents were uniformly mixed. At this point, the number of allyl groups in the polyoxyethylene having allyl attached at one end and vinyl groups in the methylvinylpolysiloxane is 0.87 per silicon-bonded hydrogen atom in the methylhydrogenpolysiloxane. Also the silicone rubber at the end of addition reaction contains 1.2% by mass of oxyethylene units. Further, the composition at the end of addition reaction contains only monovalent polyoxyalkylene groups. Next, 0.3 g of a toluene solution of a complex of chloroplatinic acid with vinyl-containing siloxane (platinum content 0.5% by mass) was added to the mixture, which was uniformly mixed with a glass rod. The liquid was cast into an aluminum dish so as to reach a thickness of 10 mm, and heated in a thermostat chamber at 80° C. for 3 hours, yielding a tack-free silicone rubber. A piece of about 1 g was cut out of the silicone rubber. After the mass of this rubber piece was measured, it was immersed in water for 15 hours. Thereafter the silicone rubber piece was taken out of water, wiped dry with tissue paper, and measured for its mass. A water absorption capacity was computed to be 0 g per gram of the silicone rubber piece.

[Chemical Formula 3]

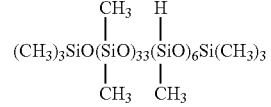

(11)

-continued $$CH_2=CHCH_2(OCH_2CH_2)_{12}OH \quad (12)$$

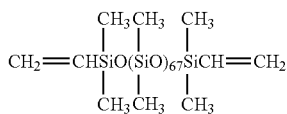
(13)

The invention claimed is:

1. Water-absorbing silicone rubber particles having a particle size in the range of 0.1 to 1,000 μm and elasticity, wherein the silicone rubber is an organopolysiloxane having polyoxyalkylene groups, contains 20 to 80% by mass, based on the silicone rubber, of oxyethylene units of —OCH$_2$CH$_2$—, and is capable of absorbing at least 10 parts by mass of water per 100 parts by mass of the silicone rubber, said polyoxyalkylene groups being (i) a monovalent polyoxyalkylene group, attached to a silicon atom in the organopolysiloxane, having the formula (1):

$$-R^1(OCH_2CH_2)_a(OCH(CH_3)CH_2)_bOR^2 \quad (1)$$

wherein $R^1$ is an alkylene group of 1 to 15 carbon atoms, $R^2$ is hydrogen, an alkyl group of 1 to 30 carbon atoms or an organic group of —(CO)—$R^3$, $R^3$ is an alkyl group of 1 to 30 carbon atoms, a is an integer of 2 to 50, and b is an integer of 0 to 15, and (ii) a divalent polyoxyalkylene group, attached to a silicon atom in the organopolysiloxane, having the formula (2):

$$-R^4(OCH_2CH_2)_c(OCH(CH_3)CH_2)_dOR^5- \quad (2)$$

wherein $R^4$ is an alkylene group of 1 to 15 carbon atoms, $R^5$ is an alkylene group of 1 to 15 carbon atoms, c is an integer of 2 to 50, and d is an integer of 0 to 15, wherein the monovalent polyoxyalkylene group of formula (1) and the divalent polyoxyalkylene group of formula (2) are present in a mass ratio in the range from 10:90 to 95:5.

2. The water-absorbing silicone rubber particles of claim 1 wherein the organopolysiloxane having polyoxyalkylene groups is obtained from addition reaction of a composition in the presence of (D) a platinum group metal based catalyst, said composition comprising (A) an organohydrogenpolysiloxane containing on average at least 3 silicon-bonded hydrogen atoms per molecule, represented by the average compositional formula (3):

$$R^6_eH_fSiO_{(4-e-f)/2} \quad (3)$$

wherein $R^6$ is a monovalent organic group of 1 to 30 carbon atoms other than an aliphatic unsaturated group, e and f are positive numbers meeting 0<e<3, 0<f≤3, and 0.1≤e+f≤3, (B) a polyoxyalkylene having a monovalent olefinic unsaturated group attached at one end, represented by the formula (4):

$$R^7(OCH_2CH_2)_a(OCH(CH_3)CH_2)_bOR^2 \quad (4)$$

wherein $R^7$ is a monovalent olefinic unsaturated group of 2 to 15 carbon atoms, $R^2$, a and b are as defined for formula (1), and (C) a polyoxyalkylene having a monovalent olefinic unsaturated group attached at both ends, represented by the formula (5):

$$R^8(OCH_2CH_2)_c(OCH(CH_3)CH_2)_dOR^9 \quad (5)$$

wherein $R^8$ and $R^9$ each are a monovalent olefinic unsaturated group of 2 to 15 carbon atoms, c and d are as defined for formula (2), wherein the number of monovalent olefinic unsaturated group in component (B) and monovalent olefinic unsaturated group in component (C) ranges from 0.5 to 2 per silicon-bonded hydrogen atom in component (A).

3. The water-absorbing silicone rubber particles of claim 1 or of claim 2, which are of spherical shape.

4. A method for preparing water-absorbing silicone rubber particles, comprising the steps of:

subjecting (A) an organohydrogenpolysiloxane containing on average at least 3 silicon-bonded hydrogen atoms per molecule, represented by the average compositional formula (3):

$$R^6_eH_fSiO_{(4-e-f)/2} \quad (3)$$

wherein $R^6$ is a monovalent organic group of 1 to 30 carbon atoms other than an aliphatic unsaturated group, e and f are positive numbers meeting 0<e<3, 0<f≤3, and 0.1≤e+f≤3, and (B) a polyoxyalkylene having a monovalent olefinic unsaturated group attached at one end, represented by the formula (4):

$$R^7(OCH_2CH_2)_a(OCH(CH_3)CH_2)_bOR^2 \quad (4)$$

wherein $R^7$ is a monovalent olefinic unsaturated group of 2 to 15 carbon atoms, $R^2$ is hydrogen, an alkyl group of 1 to 30 carbon atoms or an organic group of —(CO)—$R^3$, $R^3$ is an alkyl group of 1 to 30 carbon atoms, a is an integer of 2 to 50, and b is an integer of 0 to 15, to addition reaction in the presence of (D) a platinum group metal based catalyst, mixing the reaction product with (C) a polyoxyalkylene having a monovalent olefinic unsaturated group attached at both ends, represented by the formula (5):

$$R^8(OCH_2CH_2)_c(OCH(CH_3)CH_2)_dOR^9 \quad (5)$$

wherein $R^8$ and $R^9$ each are a monovalent olefinic unsaturated group of 2 to 15 carbon atoms, c is an integer of 2 to 50, and d is an integer of 0 to 15, dispersing the resulting dissolved liquid in (E) an insoluble liquid, and thereafter allowing addition reaction to take place under the action of the platinum group metal based catalyst (D), for curing into a rubber state.

* * * * *